(12) United States Patent
Ganey et al.

(10) Patent No.: US 11,116,872 B2
(45) Date of Patent: *Sep. 14, 2021

(54) INFUSED DEMINERALIZED BONE FIBERS

(71) Applicant: Vivex Biologics Group, Inc., Atlanta, GA (US)

(72) Inventors: Timothy Ganey, Tampa, FL (US); Tracy Scott Anderson, Atlanta, GA (US); Harry Thomas Temple, Miami, FL (US)

(73) Assignee: Vivex Biologies Group, Inc., Atlanta, GA (US)

( * ) Notice: Subject to any disclaimer, the term of this patent is extended or adjusted under 35 U.S.C. 154(b) by 508 days.

This patent is subject to a terminal disclaimer.

(21) Appl. No.: 15/999,087

(22) Filed: Aug. 17, 2018

(65) Prior Publication Data
US 2020/0054789 A1  Feb. 20, 2020

(51) Int. Cl.
*A61L 27/36* (2006.01)
*A61L 27/50* (2006.01)
(Continued)

(52) U.S. Cl.
CPC ...... *A61L 27/3608* (2013.01); *A61B 17/1635* (2013.01); *A61L 27/3604* (2013.01);
(Continued)

(58) Field of Classification Search
CPC .............. A61L 27/3608; A61L 27/3604; A61L 2430/02; A61L 27/50; A61L 27/505;
(Continued)

(56) References Cited

U.S. PATENT DOCUMENTS 5,073,373 A * 12/1991 O'Leary ............... A61L 27/227
424/422
9,387,094 B2 * 7/2016 Manrique ............... A61F 2/442
(Continued)

OTHER PUBLICATIONS

Coll et al, Diffusion of Protease into Meat for Solubility Improvement and Possible Inactivation of the BSE Prion, PLoS One, 2(2), e245, 7 pages. (Year: 2007).*
(Continued)

*Primary Examiner* — Carlos A Azpuru
(74) *Attorney, Agent, or Firm* — David L. King

(57) ABSTRACT

A method of making infused bone fibers employs the following steps: cutting or shaving whole bone into bone fibers, washing the bone fibers, demineralizing or decalcifying at least partially the whole bone or bone fibers and infusing the bone fibers with a supernatant of biologic material or a polyampholyte cryoprotectant or a combination of both to create infused bone fibers. The step of infusing includes exposing the bone fibers to a negative pressure or vacuum to draw the supernatant and/or the polyampholyte cryoprotectant into the bone fibers, or alternatively, exposing the demineralized whole bone to a positive pressure to drive the supernatant and/or the polyampholyte cryoprotectant into the bone. The resultant method creates an infused bone grafting composition having bone fibers taken from whole bone, demineralized or decalcified at least partially and infused with one or more of a supernatant of biologic material or a polyampholyte cryoprotectant or both.

5 Claims, 16 Drawing Sheets
(15 of 16 Drawing Sheet(s) Filed in Color)

(51) Int. Cl.
  *A61B 17/16* (2006.01)
  *A61L 27/24* (2006.01)
  *A01N 1/02* (2006.01)
(52) U.S. Cl.
  CPC ............ *A61L 27/50* (2013.01); *A01N 1/0221* (2013.01); *A01N 1/0284* (2013.01); *A61L 27/24* (2013.01); *A61L 2430/02* (2013.01)
(58) Field of Classification Search
  CPC .. A01N 1/0284; A01N 1/0221; A01N 1/0289; A01N 17/1635
  See application file for complete search history.

(56) References Cited

U.S. PATENT DOCUMENTS

| | | | |
|---|---|---|---|
| 9,675,644 B2* | 6/2017 | Weston | A61L 27/446 |
| 2016/0296668 A1* | 10/2016 | Burden, Jr. | A61L 27/54 |

OTHER PUBLICATIONS

Matsumura et al, Polyampholytes as Cryoprotective Agents for Mammalian Cell Cryopreservation, Cell Transplantation, vol. 19, pp. 691-699. (Year: 2010).*

* cited by examiner

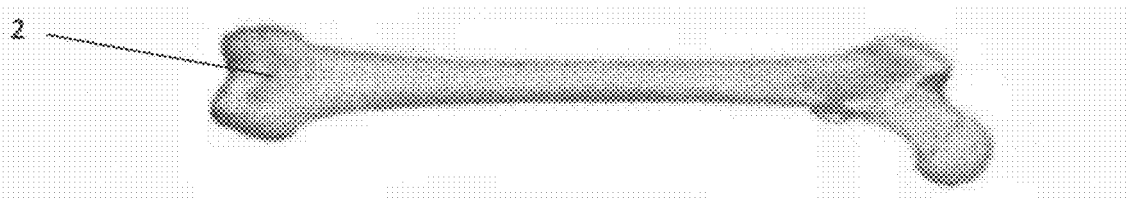
FIG. 1A
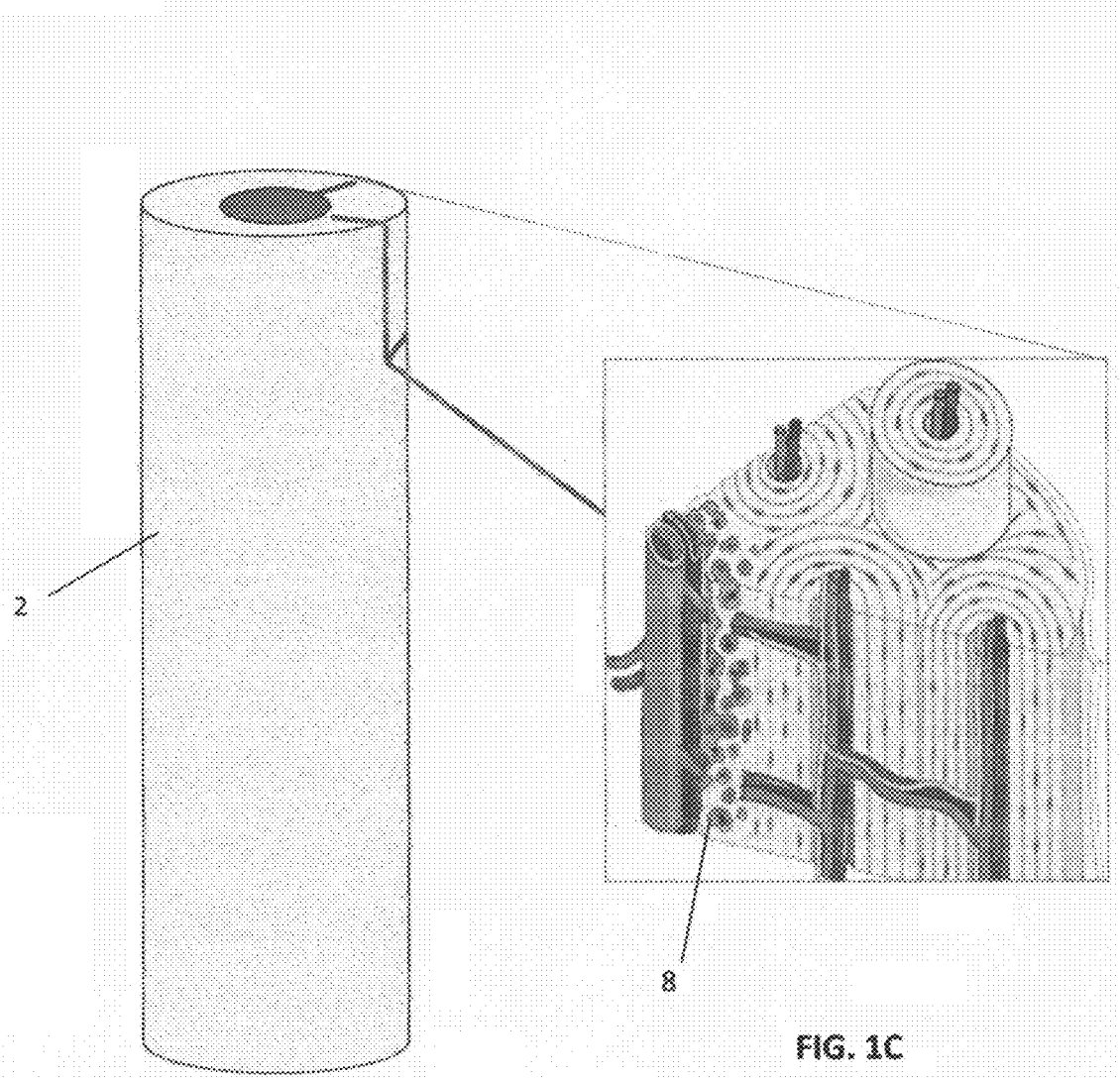
FIG. 1B
FIG. 1C

End-on Bone
Plain Sawn

INFUSED DEMINERALIZED BONE FIBERS

TECHNICAL FIELD

This invention is a bone grafting composition and method of manufacturing made from bone fibers or bone fiber mixtures infused with an acellular biologic material and/or a cryoprotectant.

BACKGROUND OF THE INVENTION

Bone grafting utilizing bone allografts and autografts to repair bone defects and voids are well known.

The bone fillers often are made in the form of bone particles or even long bone fibers and either alone or along with other materials are packed into a bone void in an attempt to achieve new bone growth.

These constructs as described in U.S. Pat. No. 9,636,436 B2 entitled "Compositions Of And Methods For Cancellous Bone Matrix" teach building a cancellous bone structure called a matrix made in the form of a porous mat that can hold demineralized bone particles. The matrix can be coated to retain the bone particles.

As in all the bone repair compositions, the goal is to achieve enhanced bone repair by stimulating new bone growth to more rapidly fill the bone void and repair the bone detect.

The present invention achieves this objective using bone fibers that are infused with an acellular biologic material and/or a cryoprotectant to enhance new bone growth. These and other objectives are explained hereinafter.

SUMMARY OF THE INVENTION

A method of making infused demineralized bone fibers employs the following steps: cutting or shaving whole bone into bone fibers, washing the bone fibers, demineralizing the bone fibers and infusing the demineralized bone fibers with a supernatant of biologic material or a polyampholyte cryoprotectant or a combination of both to create infused demineralized bone fibers.

In one embodiment, the step of demineralizing the bone fibers is replaced to accommodate a surface demineralization or surface decalcification by having instead a step of at least partially demineralizing or at least partially decalcifying the cut and washed bone fibers.

In another embodiment, the steps initially have whole bone at least partially demineralized or at least partially decalcified prior to cutting or shaving the whole bone into long aspect ratio bone fibers and washing the cut or shaved bone fibers. In this embodiment, the cut or shaved bone fibers form a hone fiber mixture including quantities of one or more bone fiber types of fully decalcified or fully demineralized bone fibers, at least partially decalcified or at least partially demineralized bone fibers, or mineralized and calcified bone fibers, or a mixture of two or more of said bone fiber types.

The step of infusing includes exposing the demineralized bone fibers or the at least partially demineralized or at least partially decalcified bone fibers to a negative pressure or vacuum to draw the supernatant and/or the polyampholyte cryoprotectant into the bone fibers, or alternatively, exposing the demineralized whole bone or at least partially demineralized or at least partially decalcified whole bone to a positive pressure to drive the supernatant and/or the polyampholyte cryoprotectant into the bone fibers. The bone fibers can have a length of 1 cm to 30 cm. The method may include freezing the supernatant and/or the polyampholyte cryoprotectant infused bone fibers.

The step of cutting or shaving includes passing the whole bone or the at least partially demineralized or at least partially decalcified whole bone through a cutting die to form shaped long bone fibers, wherein the shaped long bone fibers have a trapezoidal or triangular cross-section. The method may further include the step of drying the infused bone fibers, wherein the step of drying includes freeze-drying by lyophilization. The method further may include one or more of the steps of shaping, extrusion, molding or flattening the dried bone fibers into sheets to form random fiber stacked matting.

The resultant method creates an infused bone grafting composition having demineralized bone fibers or at least partially demineralized or at least partially decalcified bone fibers or a bone fiber mixture thereof taken from whole bone, demineralized at least partially demineralized or at least partially decalcified and infused with one or more of a supernatant of biologic material or a polyampholyte cryoprotectant or both wherein the supernatant is derived from one or more of a fatty and a cellular marrow. The supernatant includes a mixture of biologic material having non-whole cellular components including vesicular components and active and inactive components of biological activity, cell fragments, cellular excretions, cellular derivatives, and extracellular components, or whole cells or combinations of the non-whole cellular components and whole cells, wherein the mixture is compatible with biologic function. A volume of a polyampholyte cryoprotectant can be used to infuse the bone fibers alone or can be intermixed with the supernatant including the mixture of biologic material, wherein the polyampholyte cryoprotectant forms a three-dimensional infusion impregnating and coating externally enveloping each of the bone fibers along with each of the non-whole cellular components, if any, and each of the whole cells, if any, of the mixture of biologic material. The polyampholyte cryoprotectant can be a liquid of a polyamine polymer compound of carboxylated poly-lysine. The infusion of the bone fibers buffers inflammation, sustains regenerative potential and biologic function of the mixture during preservation and implantation.

The infused bone grafting composition with the infusion coating is configured to be metabolized after implantation after a predetermined time of three or more days up to six days.

In one embodiment, the infused bone grafting composition has the infused bone fibers randomly compressed into a matting or sheet. A plurality of the matting or sheets can be stacked to form a laminated stack, wherein each sheet or mat can have a distinct C/A ratio between nitrogen atom of the cationic polymer and carboxyl group of an anionic and stacking the sheets or mats together is configured to create a range variation of C/A ratios across the layers of the laminate to control nano-dimensions accentuating zeta potential for enhancing exosome absorption by creating a gradient of molecular potential when implanted.

The polyampholyte cryoprotectant forms a strong hydrophilic characteristic of the infusion coating to protect the non-whole cellular components if any and the contents of the whole cells if any. The mixture of biologic material is mechanically selected biologic material derived from bone marrow. The mixture of mechanically selected biologic material derived from bone marrow further includes a select number of non-whole cell fractions including one or more of exosomes, transcriptosomes, proteasomes, membrane rafts, lipid rafts. The biological mixture is predisposed to demonstrate or support elaboration of active volume or spatial geometry consistent in morphology with that of endogenous bone. The biological mixture extends regenerative resonance that compliments or mimics tissue complexity. The mixture is treated in the cryoprotectant prior to preservation or cryopreservation or freeze drying.

The cryoprotectant creates a physical or electrical or chemical gradient or combination thereof for tissue regeneration, and wherein the gradient has a physical characteristic of modulus or topography such as charge density, field shape or cyto-taxic, cryo- or chemo-taxic tendencies and/or wherein the gradient has a chemical characteristic of spatially changing compositions of density or species of functional molecules, wherein the molecules can offer a fixed catalytic function as a co-factor and/or wherein the gradient has an electrical characteristic of charge based or pH based or electron affinities that confer metastability in biologic potential.

The bone marrow mixture which is derived from a cadaver has separation-enhanced non-whole cell fractions vitality including one or more of the following: separating the fractions from cells heightens their vitality, reversing "arrest" of donors, accentuating responsive molecular coupling, matrix guarding in neutralizing inflammation or providing a basis for metabolic satience by balancing stimulus for repair.

The infused bone grafting composition in one embodiment has the cryoprotectant being a cryoprotectant polyampholyte of carboxylated polylysine and wherein the percentages of carboxylation can be altered to control exosome size, matrix voltages and/or zeta potential wherein the carboxylic percentage adjustment varies, a C/A ratio, a ratio between a nitrogen atom of a cationic polymer and a carboxyl group representing a anionic, wherein the zeta potential for enhancing exosome absorption is achieved by creating a gradient of molecular potential by adjusting the carboxyl ratio of the protectant. The regenerative resonance occurs in the presence or absence of a refractory response. The cryopreservation occurs at a temperature that is sub-freezing. The cryopreservation temperature is from 0 degrees C. to −200 degrees C. The mixture creates a physical or electrical or chemical gradient or combination thereof for tissue regeneration. The gradient can be a physical characteristic such as modulus or topography. The gradient can be a chemical characteristic such as spatially changing compositions of density or species of functional molecules. The gradient can be an electrical characteristic such as charge based or pH based. The biological mixture contains organelle fragments. The infused bone grafting composition may have the electrical characteristic such as a positive zeta potential formed in the infused composition to ensure uptake of nano-particles into cells when implanted as a result of a positive surface charge causing an electrostatic interaction between negatively charged cellular membranes and the positively charged infused bone fibers. The infused bone grafting composition can be maintained at ambient temperature prior to freeze drying.

The infused bone grafting composition in one embodiment has the bone fibers infused with a polyampholyte cryoprotectant for direct implantation wherein said protectant is a 1-50 w/w % aqueous solution of at least one polyamine polymer compound comprised of at least one polymer of units having side-chain amino groups, said at least one polymer of units being selected from a group consisting of ε-poly-L-lysine, α-poly-L-lysine, poly-arginine, allylamine polymer and partially methoxy-carbonylated allylamine polymer; and 50-99 mol % of amino groups, other than those forming amino-acid-to-amino-acid linkages, of said at least one polymer compound is blocked with carboxylic anhydride to form pendant moieties, each of which is linked to main chain of the polymer via an amide linkage and essentially has a not-blocked carboxylic group. Said protectant liquid is obtained by dissolving the at least one polyamine polymer compound in a physiological solution, wherein the physiological solution is a saline, Dulbecco-modified eagle MEM culture medium (DMEM), or a culture medium for cells or tissues. Said at least one polymer compound is ε-poly-L-lysine having number-average molecular weight in a range of 1000-20,000 and wherein remaining side-chain amino groups or remaining side-chain and terminal amino groups of the at least one polymer compound are not blocked by covalent bonding.

Definitions

Abbreviations: C/A ratio, ratio of cationic PEI and anionic P (Asp) block; P (Asp), poly(aspartic acid); PIC, polyelectrolyte ionomer complex.

DNase—deoxyribonuclease is any enzyme that catalyzes the hydrolytic cleavage of phosphodiester linkages in the DNA backbone, thus degrading DNA.

DMEM, DMEM/LG—Dulbecco's Modified Eagle Medium, low glucose. Sterile, with: Low Glucose (1 g/L), Sodium Pyruvate; without: L-glutamine, HEPES (4-(2-hydroxyethyl)-1-piperazineethanesulfonic acid)

Dimethyl sulfoxide (DMSO) is an organosulfur compound with the formula $(CH_3)_2SO$. This colorless liquid is an important polar aprotic solvent that dissolves both polar and nonpolar compounds and is miscible in a wide range of organic solvents as well as water. It has a relatively high melting point and is not suitable for direct implantation and requires cell washing.

DPBS—Dulbecco's Phosphate Buffered Saline.

CBT-MIXER—Mixing blade for Cancellous Bone Tumbler Jar.

Chimera—A genetic chimerism or chimera (also spelled chimaera) is a single organism composed of cells with distinct genotypes.

Cold Media—Media used during the preparation of vertebral bodies for initial processing.

Cryopreserved—Tissue frozen with the addition of, or in a solution containing, a cryoprotectant agent such as glycerol, or dimethylsulfoxide, or carboxylated poly-1-lysine.

Freeze Dried/Lyophilized—Tissue dehydrated for storage by conversion of the water content of frozen tissue to a gaseous state under vacuum that extracts moisture.

Normal Saline—0.9% Sodium Chloride Solution.

Packing Media—Media used during initial processing and storage of the processed vertebral bodies prior to bone decellularization.

PBS—Phosphate Buffered Saline.

Processing Media Media used during bone decellularization that may contain DMEM/Low Glucose no phenol red, Human Serum Albumin, Heparin, Gentamicin and DNAse.

BRIEF DESCRIPTION OF THE DRAWINGS

The patent or application file contains at least one drawing/photograph executed in color. Copies of this patent or patent application publication with color drawing(s) will be provided by the Office upon request and payment of the necessary fee.

The invention will be described by way of example and with reference to the accompanying drawings in which:

FIG. 1A is a diagrammatic view of an exemplary whole bone taken from an adult femur.

FIG. 1B shows the bone of FIG. 1A cut into a bone cylinder.

FIG. 1C shows an enlarged pre-shaped section taken from the top right portion of the bone cylinder of FIG. 1B.

FIG. 4 is the step of washing the demineralized bone fibers.

FIG. 5 is the step of infusing the bone fibers with a supernatant of biologic material.

FIG. 6 is an alternate step of infusing the bone fibers with a mixture of the supernatant and a cryoprotectant.

FIG. 7 is an alternative of infusing the bone with only the cryoprotectant.

FIG. 8 is the step of lyophilization of the infused bone fibers from FIG. 6, 7 or 8.

FIG. 12B shows a range from C/A 0.125 to C/A of 8 yielding a 64 times delta or difference potential.

DETAILED DESCRIPTION OF THE INVENTION

Figure 1D:
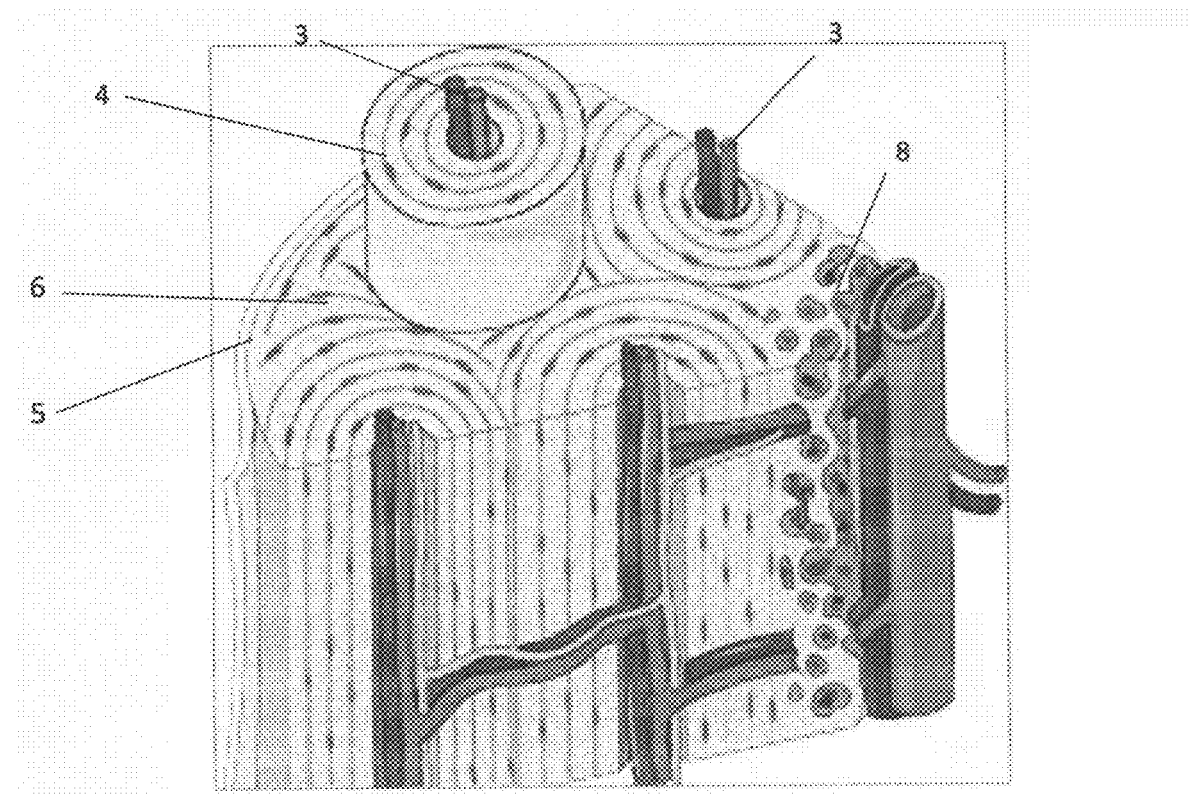
FIG. 1D is an enlarged view of the section from FIG. 1C exhibiting the directionally varying concentric features of the bone.
Figure 1E:
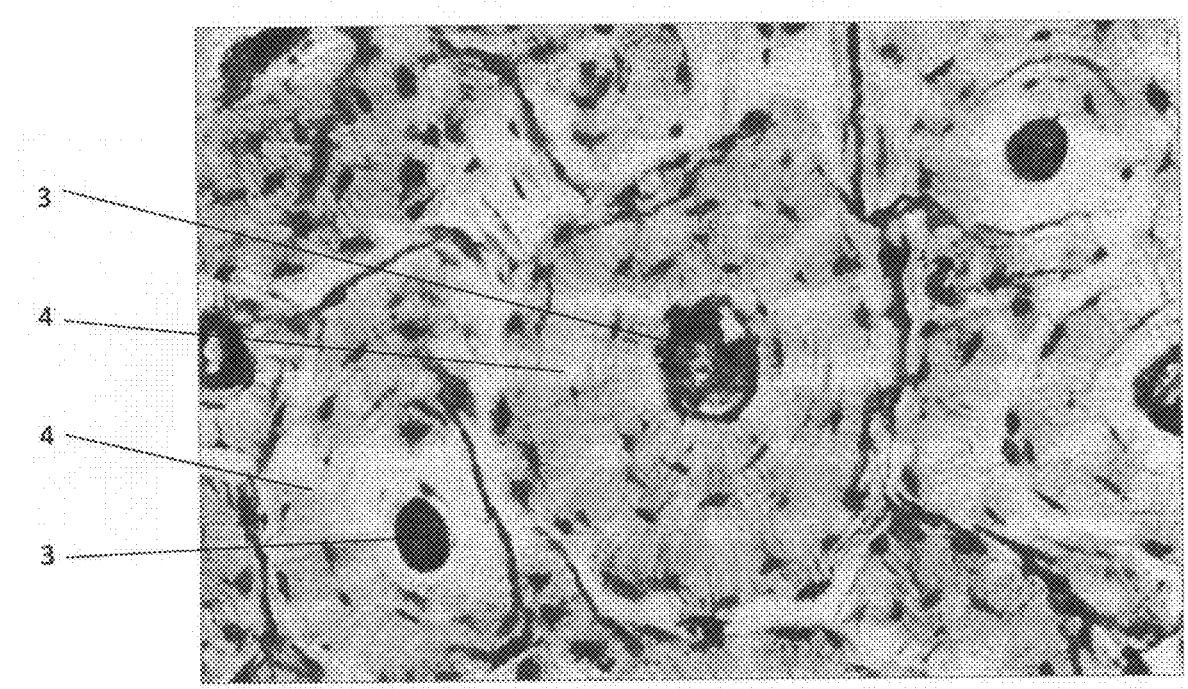
FIG. 1E is a magnification of the bone illustrating the structure of the bone formation.

The value of current bone void fillers as random compositions that have been divested of morphology similarly address the shortcomings incumbent as lack of alignment and orientation of Haversian osteons characterized by long concentric lamellar orientations. This application and invention proposes high pressure substitution of supernatant material from bone marrow that is enriched with exosomes, and micro-ma materials. In practice, the manufacturing process is designed to accommodate a decalcification step which is known, a drying step which is known in the art, but to seek a divergent interest in next steps where the material is perfused under high pressure with the supernatant rich material from bone marrow processing. This material is replete with exosomes and has bioactive properties. A second step, or a combination of steps is next offered as novel technology. By using variation in substitution of cryoprotectant, the application notes other fields of polymer research that have varied amide and carboxyl linkage to better control nano-particle, and mV electropotential in delivery devices for cancer therapy. In this specific application, the ability to use the variations in voltage to not only control size but create standing voltage differences is novel. Along with the HCTP controlled use of the basis of cryoprotectants, the value is novel nano-sizing, cell merging value, and provide infused DBM fibers with exosome value. Alternatively, the use of low pressure vacuum differentials can be used to impregnate and infuse the bone fibers with the supernatant and/or cryoprotectant.

These and other benefits of the present invention and the method of preparing it are described hereinafter.

Dr. Matsumura has developed a Cryoprotectant that substitutes carboxylation for amide groups to balance the charge. The present invention expands these features in unique ways.

Current technology is driving to smart nanomedicine that incorporates the ability to use mV variations to enhance or reduce the potency of drug delivery. A positive zeta potential of the complexes ensures the uptake of nanoparticles into cells, since a positive surface charge allows an electrostatic interaction between the negatively charged cellular membranes and the positively charged complexes.

C/A Ratio and Carboxyl Substitution, Various C/A ratios (ratio between the nitrogen atom of the cationic polymer and the carboxyl group representing the anionic)

The original Matsumura patent for carboxylated polylysine provides the range of 50-99% blockage of amide moieties and as such the potential for variations in the C/A ratio is appropriate to improvements in C/A ratio control.

The goal is to protect the potential for specifying and controlling nano-dimension, accentuating zeta potential for enhancing exosome absorption, and utilizing adjustment in the cryoprotectant for fractioning and creating gradients of molecular potential. Multi-Laminate made from sheets or mats of the infused bone fiber composition allows for nano-electrical dimension control, control of mV charge and variation between fiber entities, Zeta-potential variability, exosome sizing control, and pH response variability during wound healing.

Exosome size and matrix voltage and zeta potential can be controlled with carboxylation of the cryoprotectant. Exosome interaction is essential to the attachment of cells to matrix. Work in Migrasomes has shown specificity for exosome and matrix molecular entity.

The present invention has a clear path for exosomes from bone marrow, cryoprotectant in range that can be used to create unique mats, and a biomedical manufacturing facility to develop novel products. Short term value in matted, molded, or extruded materials, but long-term novelty in controlling electrophysical nature of advanced materials is explained herein.

With reference to FIGS. 1A-1E, various views of an adult femur bone 2 are illustrated. While the present invention is shown with an adult femur bone 2 as an example, other long bones, or other bones in general can be used to make the infused bone fiber composition 10 of the present invention. The adult femur bone 2 is provided as an example of one such bone. With reference to FIG. 1B, the ends of the bone are shown cut off leaving the diaphysis, or midsection of a long bone, forming a cylindrical bone 2. With reference to FIGS. 1C and 1D, a cross sectional segment of the bone 2 from the upper right-hand view of FIG. 1B is illustrated. In this view, blood vessels 3 are illustrated. Surrounding the blood vessels 3 are concentric lamellae 4. Around the remaining portion of the bone 2 are circumferential lamellae 5 and interstitial lamellae 6. Comprising the compact bone otherwise known as cortical bone. The center portion of the bone or spongy section is the cancellous or trabecular bone 8. The present invention uses the whole bone as illustrated, however, the whole bone is first demineralized.

Figure 2A:
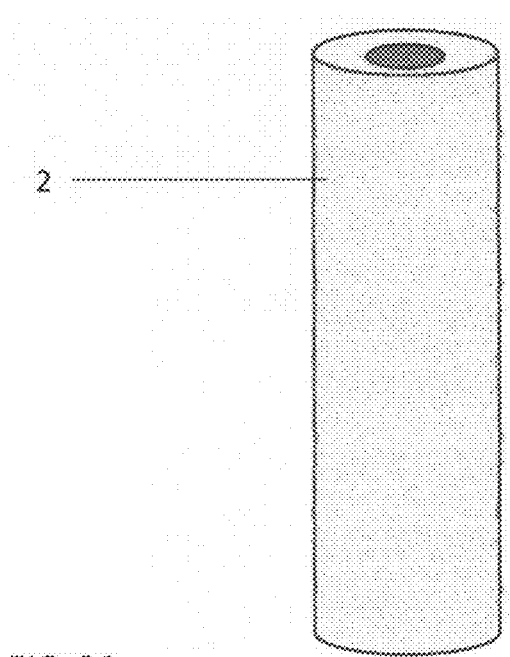
FIG. 2A is a schematic illustration of a cylindrical long bone.
Figure 2B:
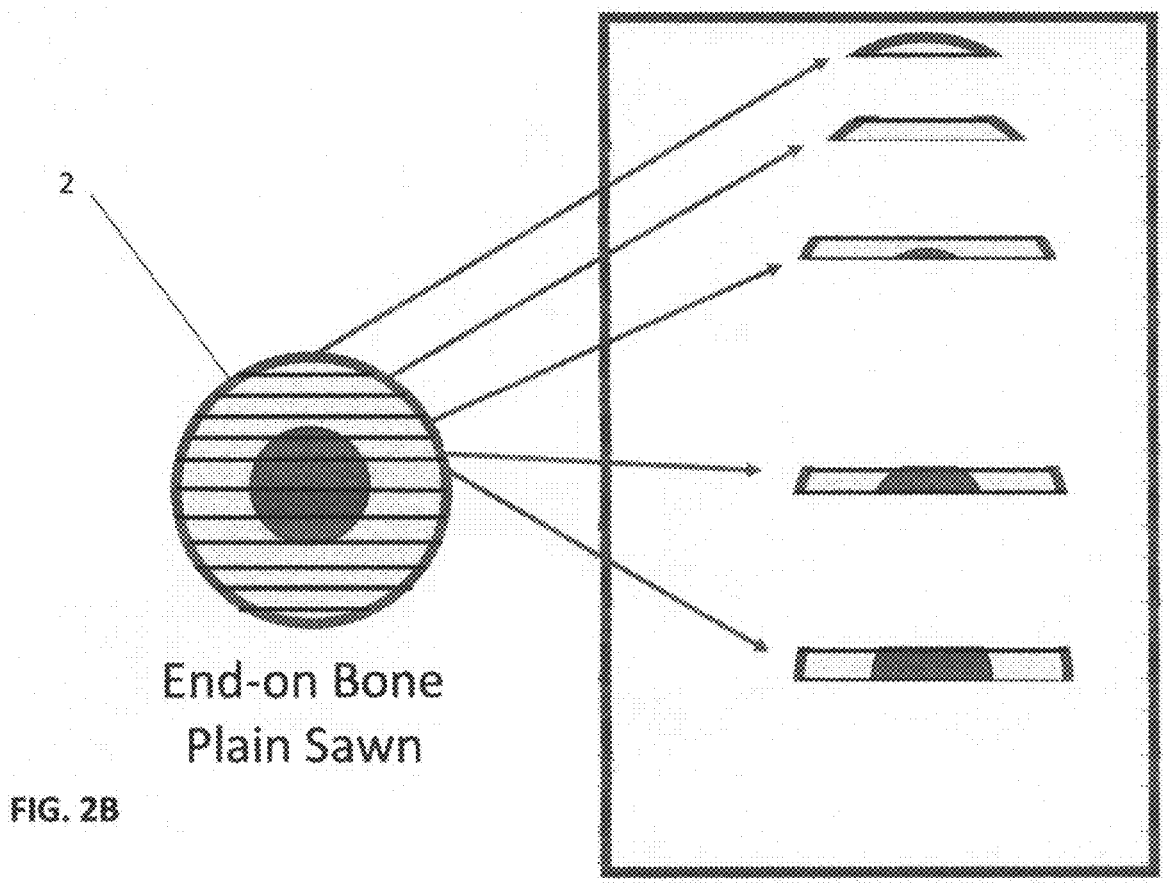
FIG. 2B is an end view of the bone of FIG. 2A showing the bone cut into thin sections down the length.
Figure 3:
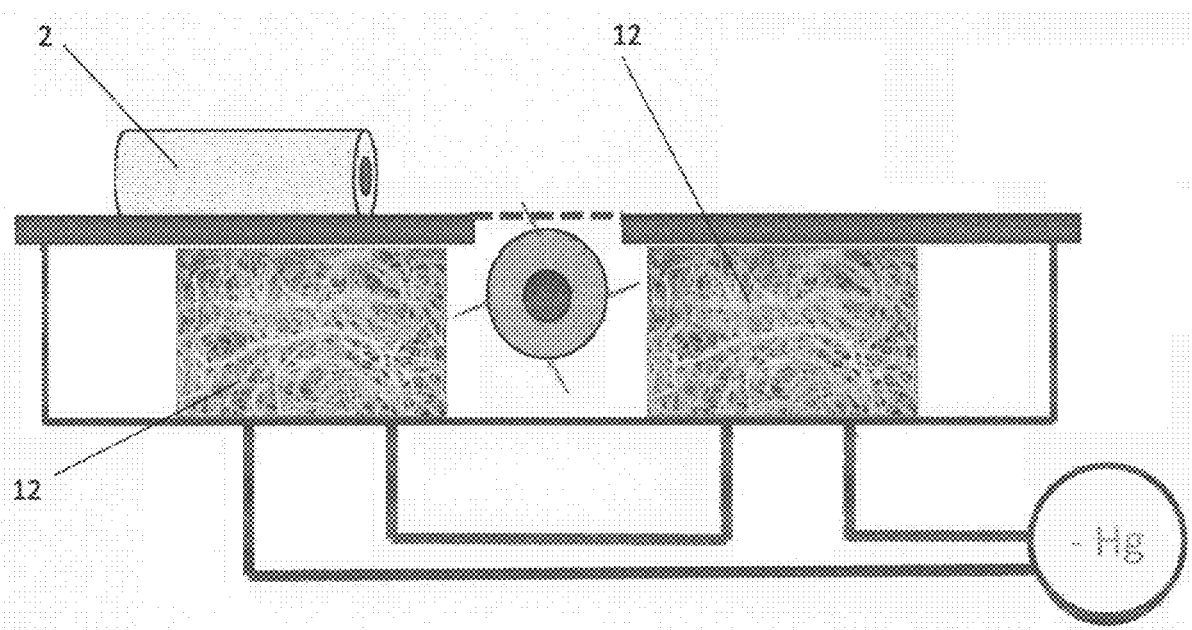
FIG. 3 is an exemplary diagrammatic view of demineralized bone cut along a plane parallel to and cutting tangent to the surface of the bone cylinder.
Figure 4:
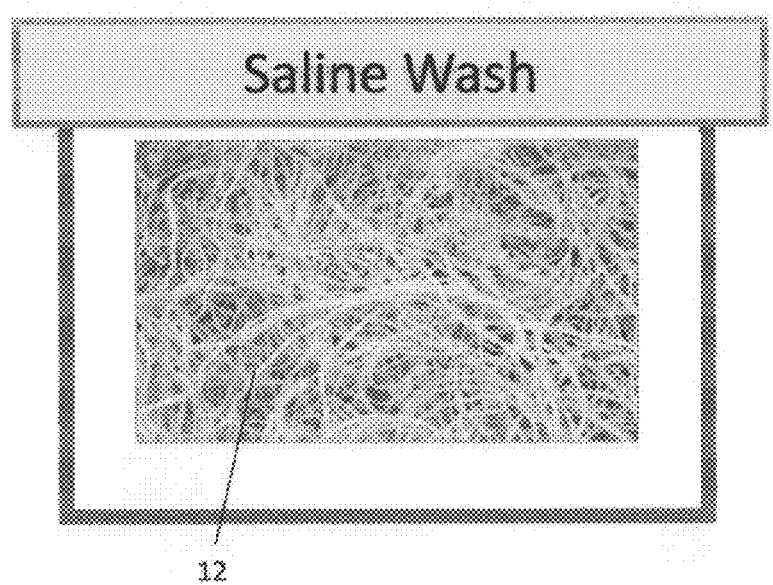
FIGS. 4-8 are views of the method steps to prepare the cut bone fibers.
Figure 5:
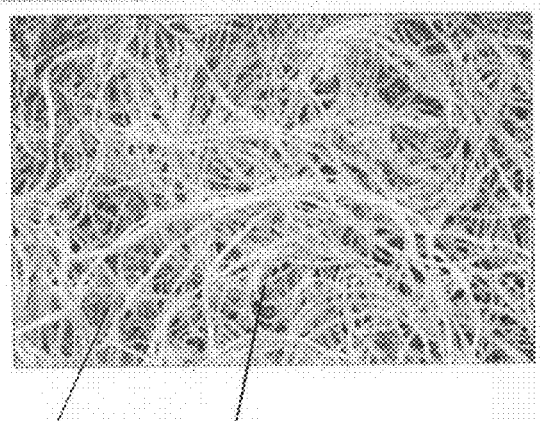
Figure 6:
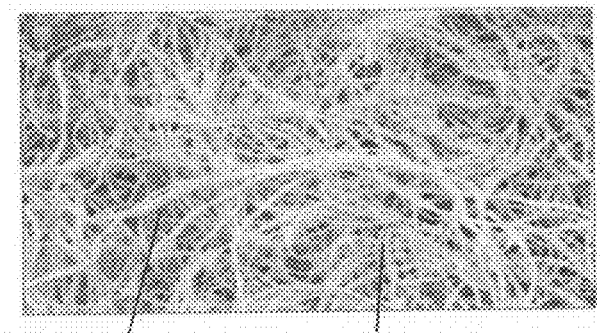
Figure 7:
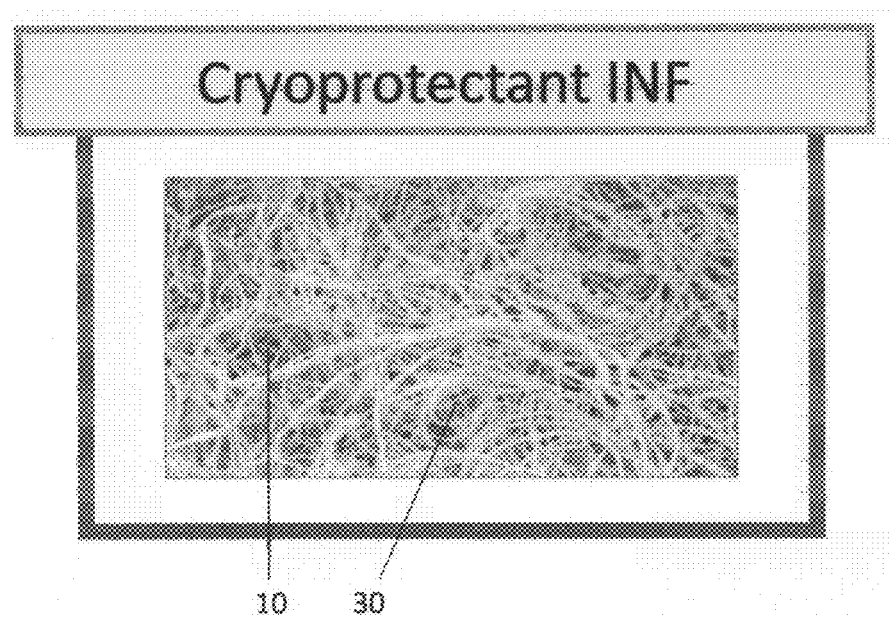

With reference to FIG. 2A, the bone 2 in cylindrical form is shown. In FIG. 2B and end view of the bone 2 is shown wherein the bone, when placed on end, can be cut such that small segments parallel to the longitudinal axis of the bone can be formed. These long segments can range in length from a few cm to 30 cm in length. With reference to FIG. 3, a planer is illustrated where the cylindrical bone can be positioned onto a table brought in line and cut to create the bone fibers 12. The bone fibers 12, when formed, as illustrated in FIG. 4 will be saline washed. Then the bone fibers 12 after being saline washed can then be infused either under pressure or under vacuum. As shown in FIG. 5, a supernatant 25 infusion is provided to the bone fibers 12. As shown in FIG. 6, the supernatant 25 along with the fibers 12 can further be infused with a cryoprotectant 30. Alternatively, the bone fibers 12 can be infused with only the cryoprotectant 30.

Figure 8:
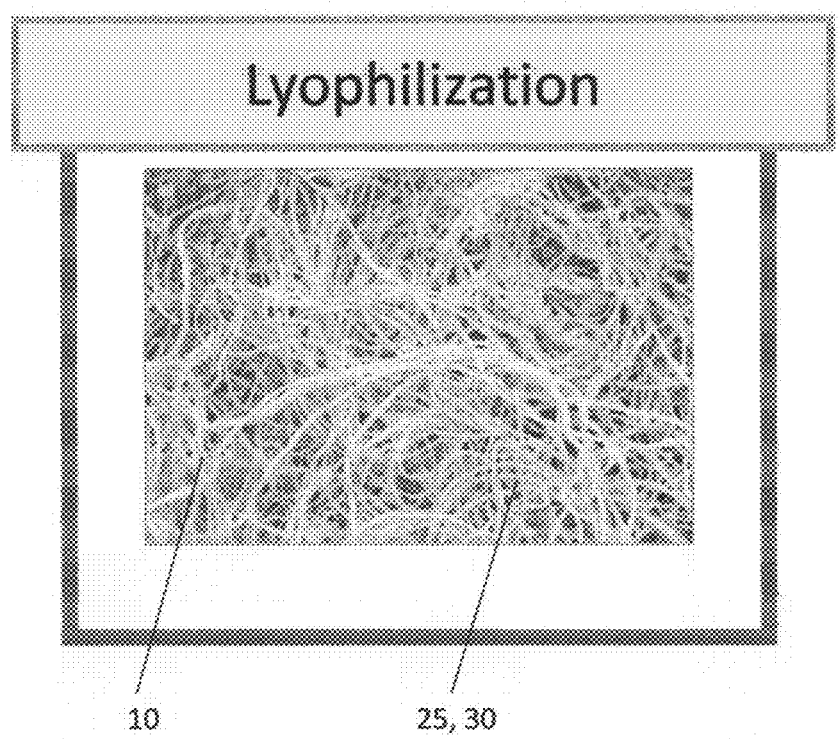

After the bone fibers 12 are infused with the supernatant 25 or cryoprotectant 30 or the combination of the supernatant 25 and the cryoprotectant 30, the infused bone fibers 10 can then be lyophilized, as illustrated in FIG. 8.

Figure 9:
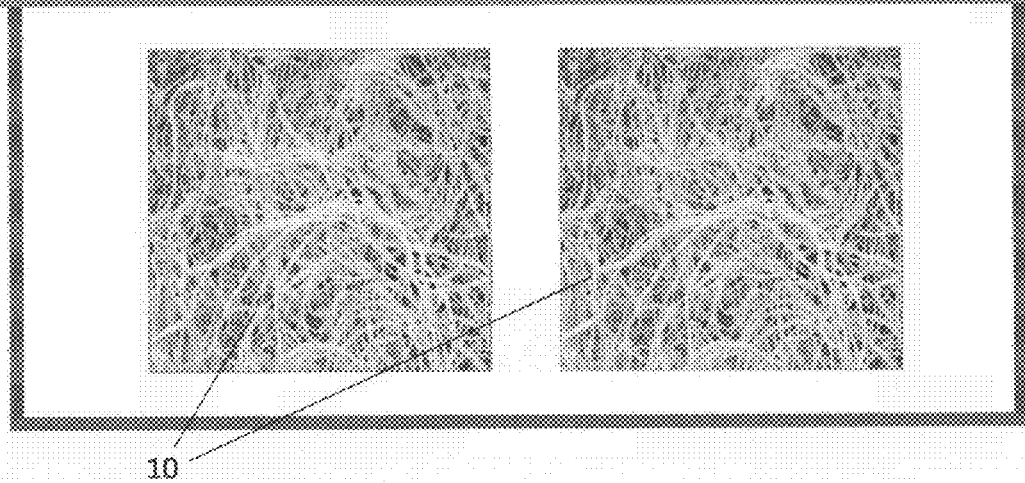
FIG. 9 illustrates forming the bone fibers into a sheet or mat using the steps of shaping, extrusion, molding or flattening.
Figure 10:
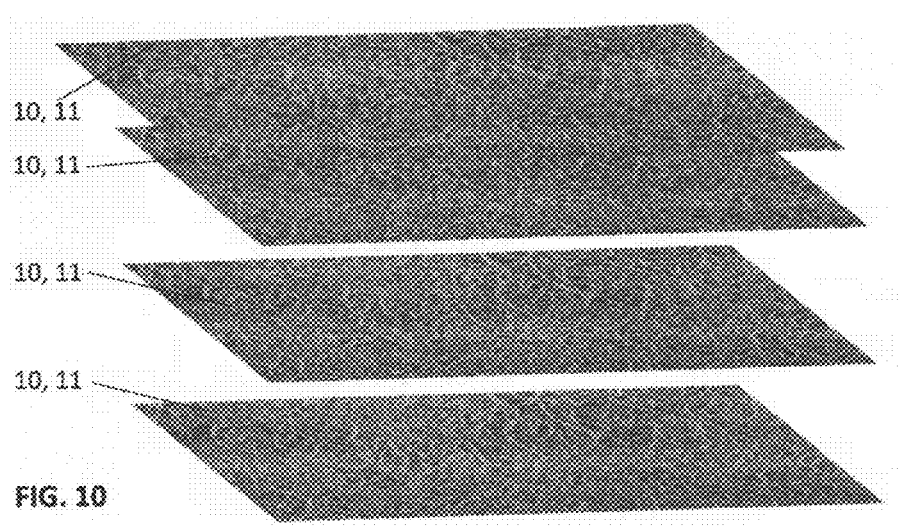
FIG. 10 schematically shows a plurality of the sheets or mats being stacked.

As shown in FIG. 9, the infused bone fibers 10 can then be shaped, by extrusion, molding or flattening. The preferred shape is mats as illustrated in FIG. 10. The mats or sheets 11 can then be combined to form a laminate 15.

Figure 11:
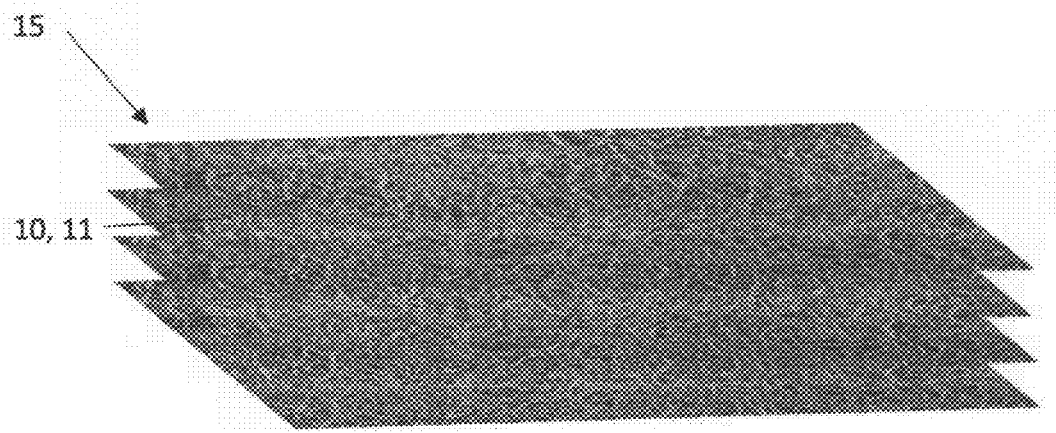
FIG. 11 schematically shows the stack being press fit.
Figure 12A:
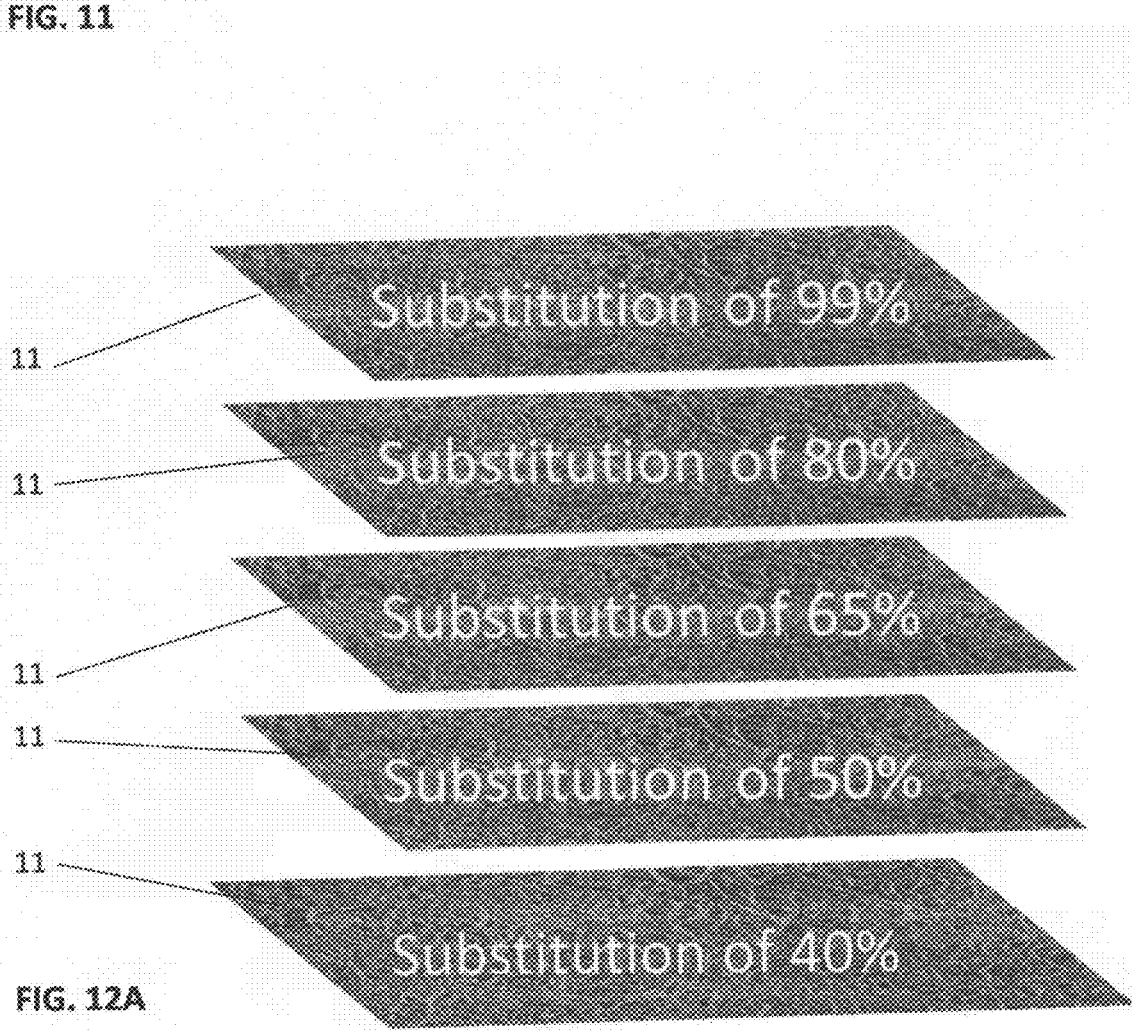
FIGS. 12A and 12B are diagrammatic views of sheets or mats with variation of C/A ratios.
Figure 12B:
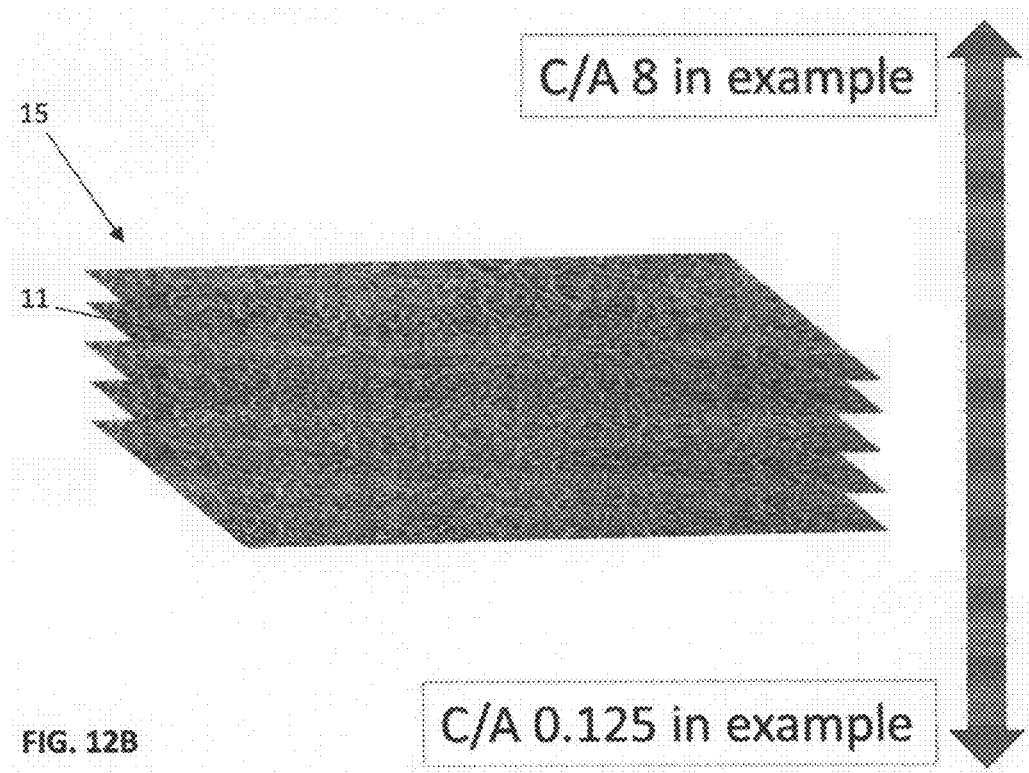
Figure 12C:
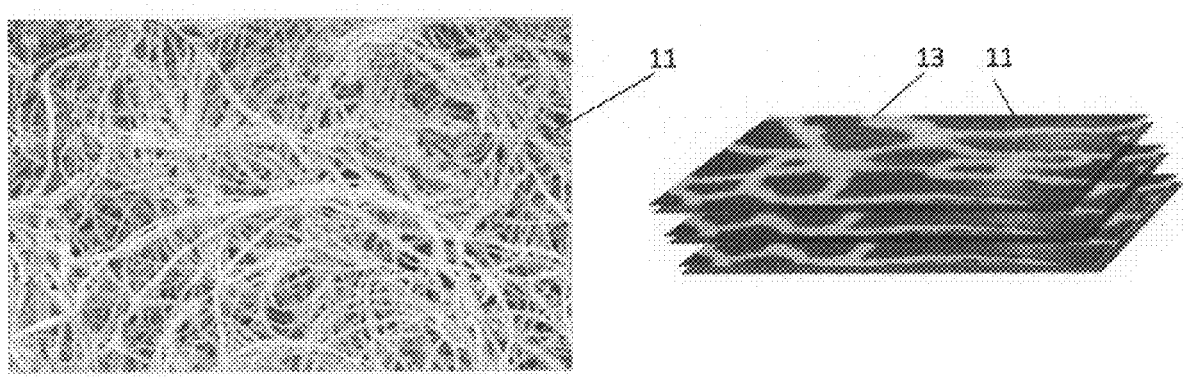
FIG. 12C is a view of a multilaminar sheet production.

As shown in FIG. 11, the laminate 15 is comprised of a plurality of sheets 11 of the infused bone fibers 10. These sheets 11, when compressed together to form the laminate 15, can be made in a unique way as illustrated in FIG. 12A. FIG. 12A represents an embodiment of the invention wherein the cryoprotectant has been adjusted in terms of its carboxylic percentage. As shown, a substitution of 40, 50, 65, 80 and 99 percent carboxylic is illustrated in FIG. 12A When this material is combined to make the laminate 15, a variation in C/A ratio can occur as illustrated in FIG. 12B. This ratio can vary in C/A from 0.125 as an example up to 8 as an example creating a wide variation in C/A ratio range available when employing this laminate. FIG. 12C shows the laminate made wherein each sheet has a pattern that has been formed on an upper surface of the sheet material 11. This pattern 13 can be a pattern of voids or mimetic pattern simulating bone if so desired.

Figure 13:
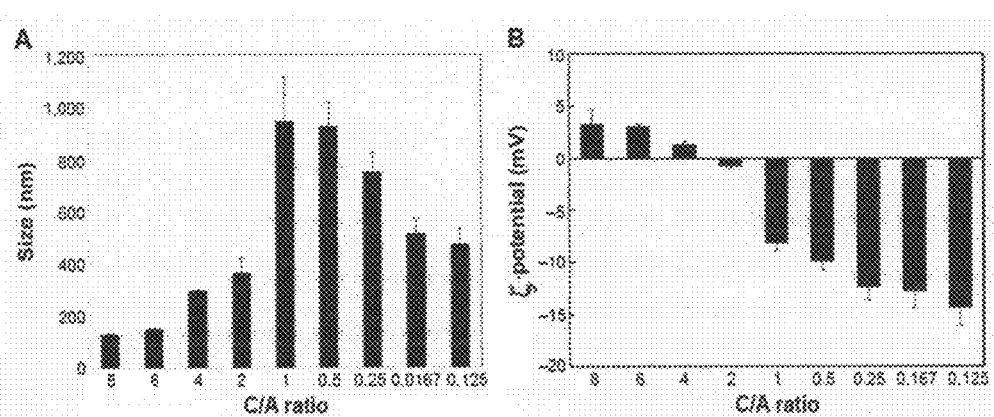
FIG. 13 is a pair of charts taken from the International Journal of Nanomedicine showing polyampholyte variation.

An important aspect of the C/A ratio variation is the different particle sizes shown in FIG. 13 that can be achieved by varying the C/A ratio. Additionally, the zeta potential B is illustrated in potential mV by a variation of the C/A ratio. By combining these two aspects, it is possible to create variations in charge and size of the particles created such as exosomes.

Figure 14:
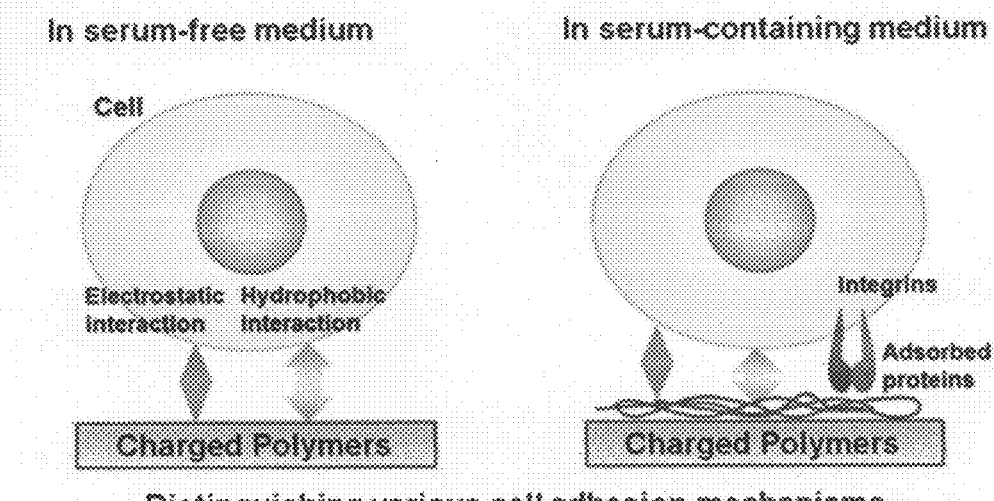
FIG. 14 is a chart showing the effects of charged polymers and cell adhesion.

FIG. 14 is an example of a serum free medium, wherein a cell is exposed to charged polymers and an electrostatic interaction and hydrophobic interaction occurs distinguishing the various cell adhesion mechanisms. Similarly, charged polymers can be provided if the polymers are charged positively and the cells have a negative charge, an absorption of proteins can be accelerated and enhanced in the serum containing medium as shown in FIG. 14.

For completeness of the understanding of the invention as described above, an example of one method of recovering the biological material from bone marrow is disclosed. It is understood that other sources and methods can be used to collect biologic material such as from bone, blood, fat cells, including the isolating of whole cells from these alternative sources from living hosts or cadavers and these cells would equally benefit from the present invention.

With reference to the exemplary method which is a tissue regenerative biological composition made from bone marrow 200, it is believed best understood by the methods used to process and recover the biological composition, as illustrated in the FIGS. 15-20.

Figure 15:
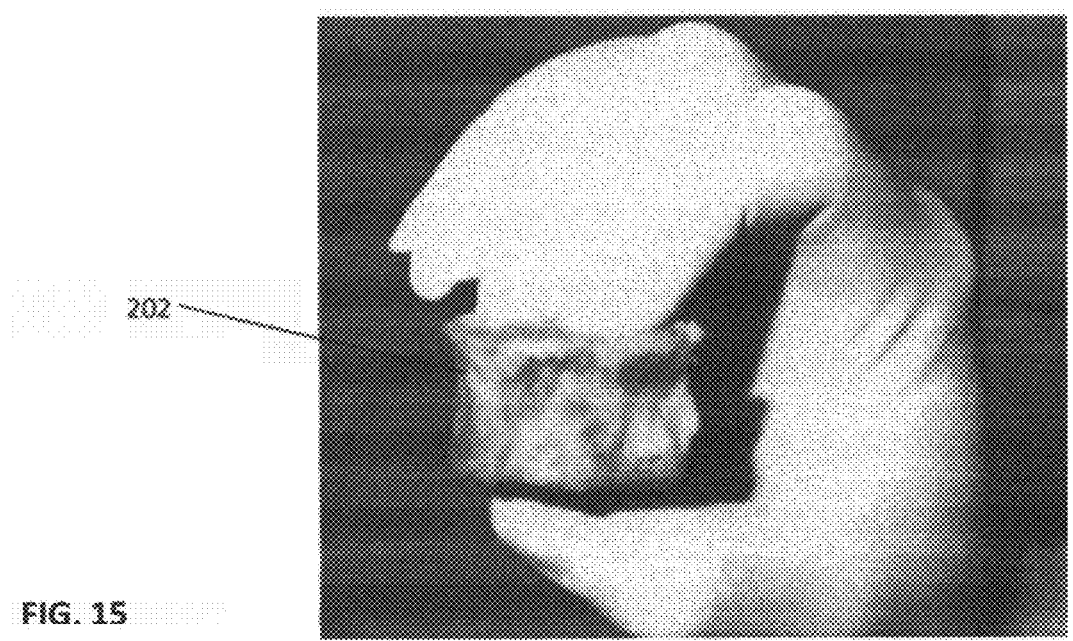
FIG. 15 shows a photograph of a cut vertebral body taken from a spine of a cadaver donor.
Figure 16:
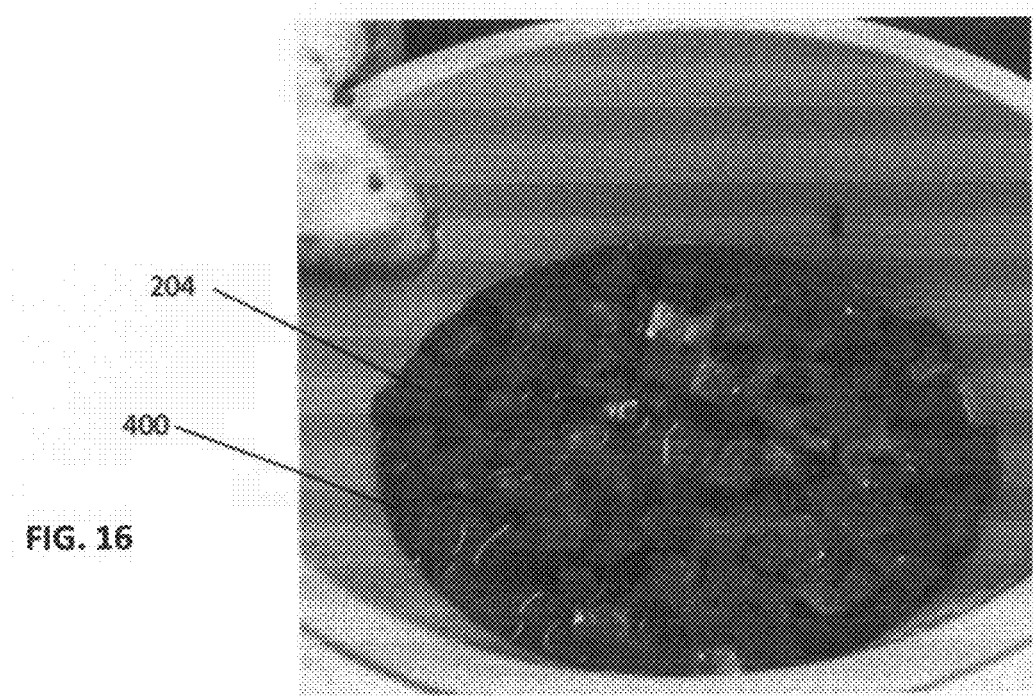
FIG. 16 shows a photograph of the vertebral body after being cut into cubic pieces and immersed in a packing media.
Figure 17:
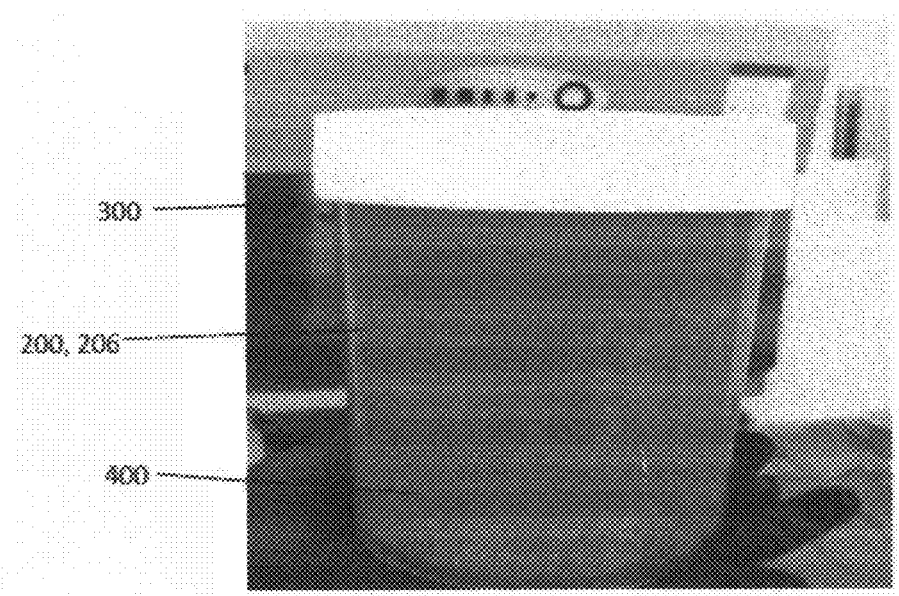
FIG. 17 shows a photograph of the bulk bone material after being ground and immersed in packing media and placed in a jar for later tumbling.
Figure 18:
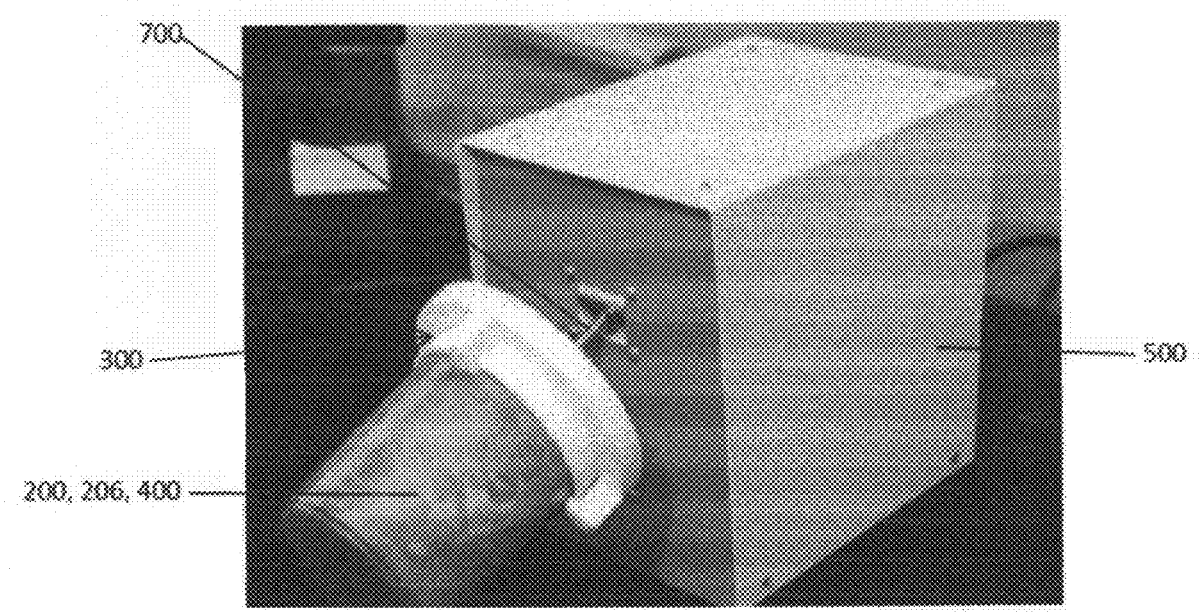
FIG. 18 shows a photograph of the jar with a CBT-Mixer connected to a tumbler.

The first steps are to collect, recover and process bone marrow 200 from a cadaver donor. To do this, the spine is removed aseptically from the cadaver and the resultant spine segment is covered by cold media. The cold media has 0.5 ml of Heparin; 10,000 units/ml per 500 ml of DMEM. DMEM is a sterile solution with low glucose (1 g/L), Sodium Pyruvate; without L-glutamine, or HEPES. This cold media is used for packaging the spine segments for later processing. At this point the spine segment includes a plurality of vertebral bodies 202. The clinical technician must remove as much soft tissue as possible and cut each vertebral body 202 with a saw. These vertebral bodies 202, once cleaned, of all adherent soft tissue around the cortical surfaces will look as shown in FIG. 15.

Once a cleaned vertebral body 202 is obtained, the next step involves cutting each vertebral body 202 into pieces, each piece 204 roughly 1 cm$^3$. The cut pieces 204 being immersed in a packing media 400. The exemplary packing media can be DMEM with 0.5 ml Heparin and 1.25 ml of DNAse added.

Once all the vertebral bodies 202 have been cut, the pieces 204 are taken to the bone grinder. The bone is ground into 4-10 mm pieces using packing media 400 to help the pieces go through the grinder. The ground bone 206 (bulk cortical-cancellous crushed) and all of the packing media 400, estimated volume of 500 ml are transferred into a jar 300 where 0.5-1.0 ml of Gentamicin is added to the jar 300 with ground bone 206 and packing media 400. At this point, the crushed bone 206, including cellular soft marrow 200, is intermixed.

Figure 19:
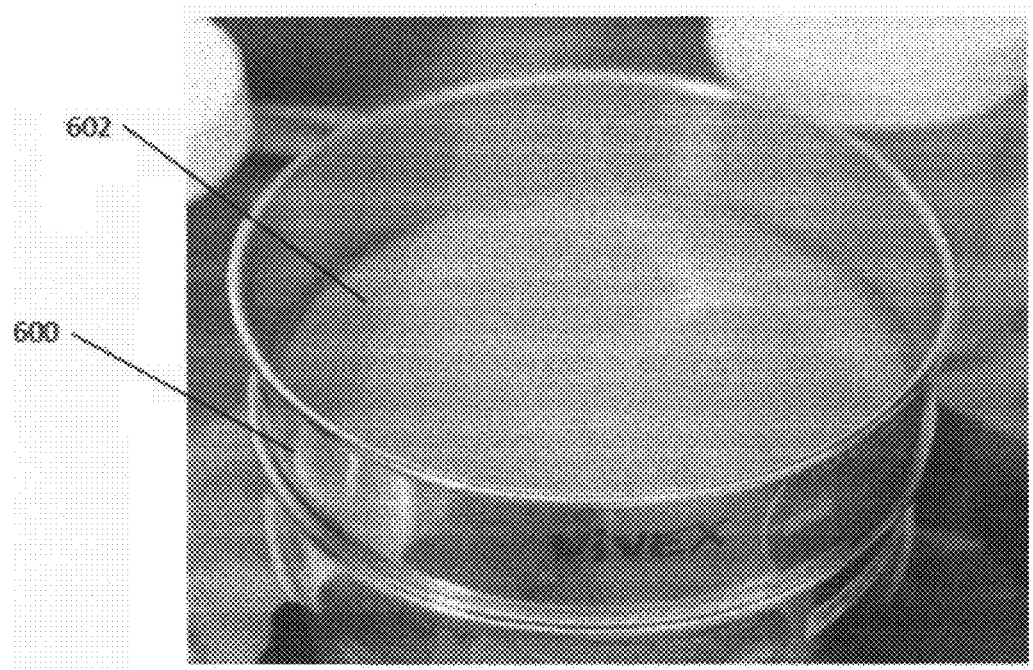
FIG. 19 is a photograph of an exemplary sieve device having sieves sized to separate the solid material.

The step of mechanically separating these cellular components of bone marrow 200 from the cadaverous bone is next performed. Transferring the bulk cortical-cancellous bone chips into a new jar with a CBT-Mixer in the jar. The bulk cortical-cancellous bone chips 206 will go through four cycles as summarized in the table below. Each cycle, after cycle 1, contains three steps using a bone tumbler 500 and sieve set 600. The sieve set 600 has screens 602 of various sizes, for example 500 µm and 180 µm, as shown in FIG. 19.

| Step | Cycle 1 | Cycle 2 | Cycle 3 | Cycle 4 |
|---|---|---|---|---|
| Bone Tumbler | 30 minutes. Using 500 mL Processing Media | 30 minutes Using 500 mL Processing Media | 30 minutes Using 500 mL Processing Media | 30 minutes Using 400 mL Processing Media |
| Sieve Set | Use the 500-µm, and the bottom pan sieve. Discard decanted fluid. | Use the 500-µm, 180-µm and bottom pan sieve. Collect decanted fluid. | Use the 500-µm, 180-µm and bottom pan sieve. Collect decanted fluid. | Use the 500-µm, 180-µm and bottom pan sieve. Collect decanted fluid. |
| Centrifuge | N/A | Use decanted fluid. | Use decanted fluid. | Use decanted fluid. |

Figure 21:
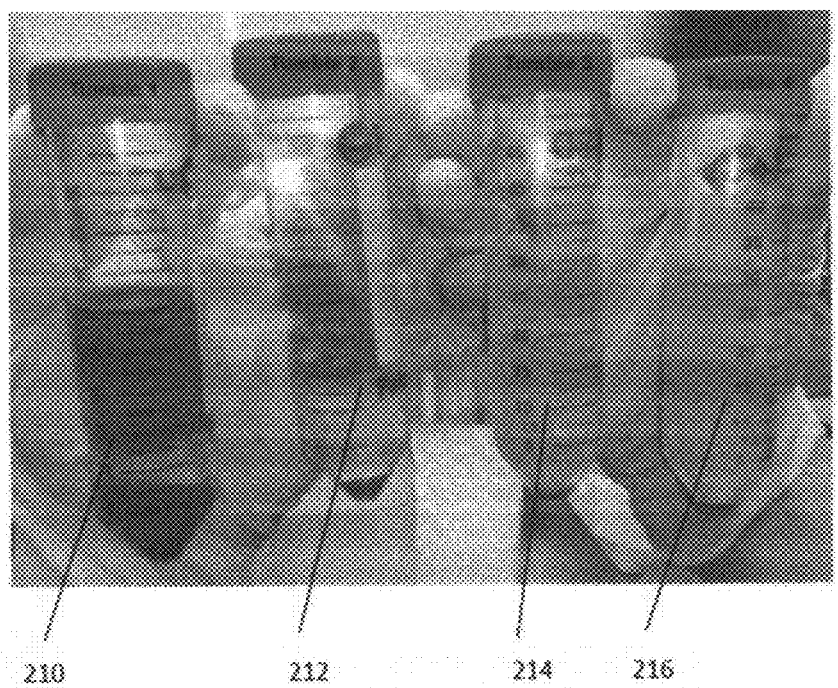
FIG. 21 is a photograph showing the four tumbling steps 1-4 by exemplary collection and Ficoll separation of the decanted fluids, the fluid in tumble 1 being completely discarded to remove unwanted debris.

In cycle 1, the decanted fluid 210 is discarded. To best understand this, an exemplary FIG. 21 shows conical tubes with the decanted fluids after each cycle followed by Ficoll separation. Tumble 1 or Cycle 1 has most of the unwanted cells and debris as evidenced by its dark and red appearance whereas each subsequent cycle 2, 3 and 4 are progressively cleared. This FIG. 21 is only to illustrate the effects of multiple tumbles 1-4 and the value in discarding the decanted liquid 210 after the first tumble 1.

After each subsequent sieving of the bulk bone material 206, the decanted fluid 212, 214, 216 containing the mixture with whole cells is collected and put into a collection jar. When the next three cycles are complete and the decanted fluid is all placed in the collection jar comingling the fluids 212, 214 and 216 to form a decanted fluid 220. Then the centrifugation of the combined decanted fluid 220 occurs by placing the fluid 220 in a number of 250 ml conical tubes using a 100 ml pipette. The centrifuge is programmed to 280×g for 10 minutes at room temperature, preferably about 20 degrees C. The fluid 220 is passed through a blood filter to further remove any bone or spicules or clumps from the suspended cells. This completes the step of centrifuging and filtering. At this point, the mixture including whole cells 240 has been separated from the soft marrow tissue 200 and the remaining cancellous and cortical bone is discarded.

Figure 20:
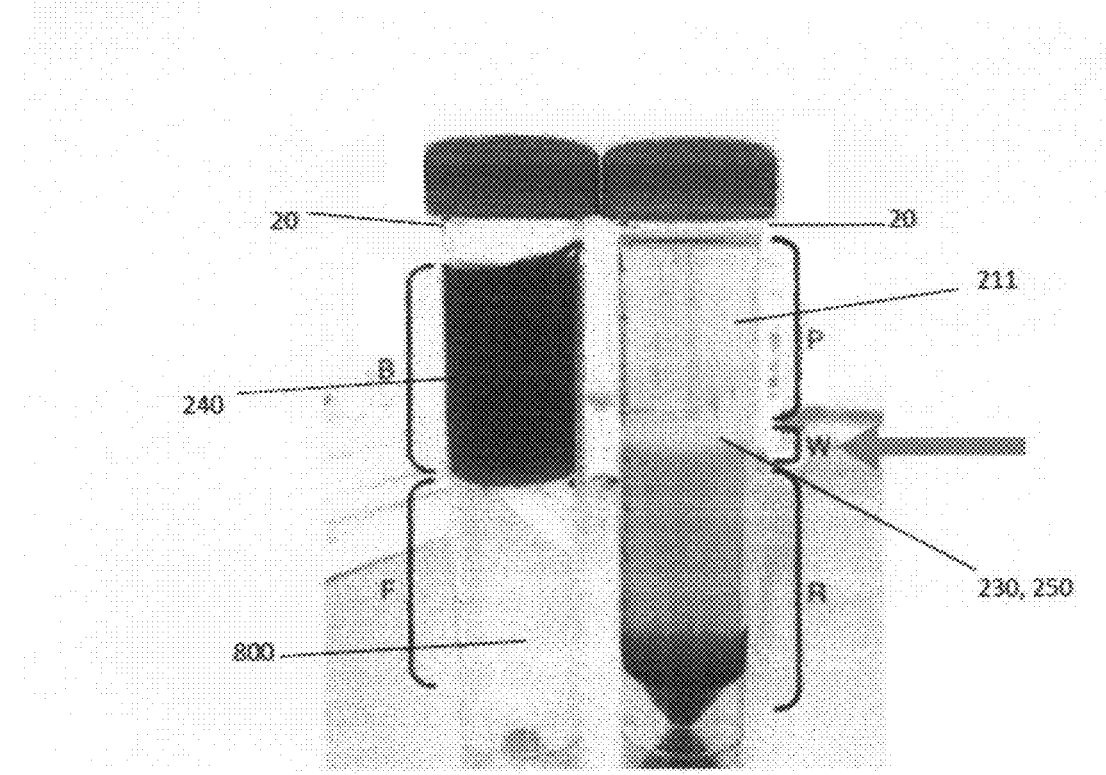
FIG. 20 shows a photograph of two 50-ml vials, the one on the left being prior to centrifuging with the Ficoll that is commercially available at the bottom and the material above it. The 50-ml vial on the right is after centrifuging showing the non-whole cell fraction interface layer.
Figure 22:
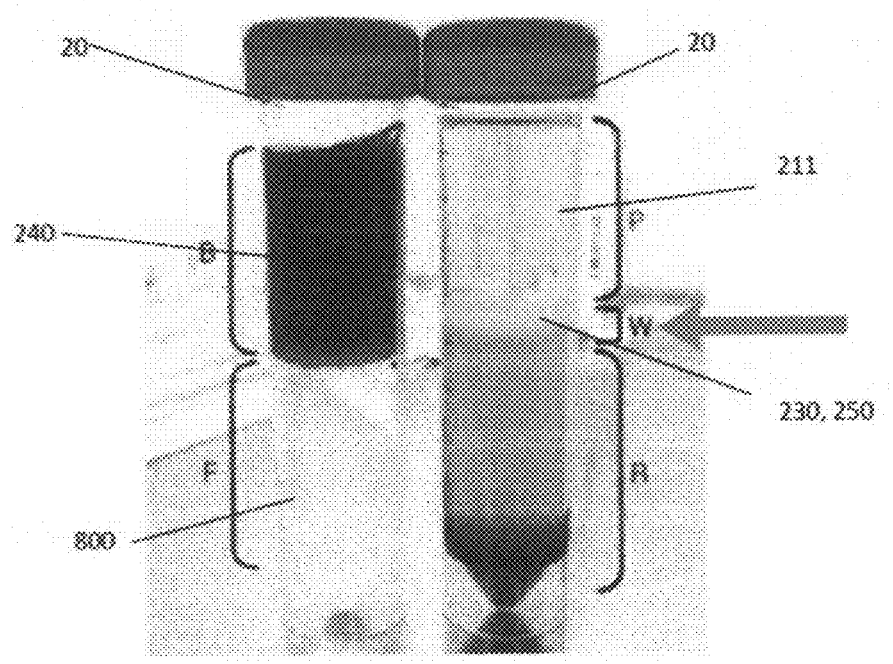
FIG. 22 shows a photograph of two 50 ml vials, the one on the left being prior to centrifuging with a sucrose gradient that is commercially available at the bottom and the material above it. The 50-ml vial on the right is after centrifuging showing the non-whole cell fraction above the interface layer.

After this, as shown in FIGS. 20 and 22, the step of separating the cells 240 from the non-whole cellular components can occur by a density centrifugation, if so desired. The whole cells 240 are in the interface, often called the buffy layer, and the non-whole cell components are in the supernatant above the interface. The mixture is placed in 50 ml conical tubes 20 with Ficoll 800 and undergoes a Ficoll-Paque separation under centrifugation wherein a cell density gradient is established by spinning at 400×g for 30 minutes at room temperature, preferably about 20 degrees C. The mixture includes cellular or non-cellular components or a combination thereof. All fluid 211 above the interface 230 can be removed which includes the desired non-whole cell components and which excludes the whole cells 240, 250 or all the fluid 211 and the interface 230 can be removed together.

Typically, non-whole cell fragments, or membrane components have a diameter of 40-100 nm and can be separated within a density of 1.13-1.19 g/mL in a sucrose solution, and can be sedimented by centrifugation at 100,000 g. In fact, these fragments, or cell fractions, or microvesicles, have been collectively referred to as exosomes. Ranging in size from 20-1000 nm in diameter, they have been similarly referred to as nanoparticles, microparticles, shedding microvesicles, apoptotic blebs, and human endogenous retroviral particles. There are few firm criteria distinguishing one type of microvesicle from the other.

Following removal of the cell fraction, the supernatant is further filtered through 0.45 and 0.2 µm filters. Exosomes are further collected and separated within the suspension in multiple centrifugation steps with increasing centrifugal strength to sequentially pellet cells (300 g), microvesicles (10,000 g) and ultimately exosomes (100,000 g). Cells can be deliberately removed to achieve a mixture having the non-whole cell fragments and microvesicles or can be kept forming a combination of whole cells and non-cellular components. An important aspect of the invention is the use of the supernatant with the buffy layer or interface with whole cells and be used together. In practice, the survival of the whole cells is not particularly relevant as the contents of the whole calls can be captured when the membrane of the whole cell is ruptured during processing. The cellular contents are bioactive, some as the acellular biologic material in the supernatant above the interface. All of these constituent elements can be used to form the biological mixture if so desired.

Subsequent separation using density gradient-based isolation, using sucrose or commercially available prep can be applied to obtain more pure exosome preparations. Recent reports encouraging the use of iodixanol-based gradients for improved separation of exosomes from viruses and small apoptotic bodies are considerations left open to be adopted or adapted in refinement. Differing from sucrose, iodixanol forms iso-osmotic solutions at all densities, thus better preserving the size of the vesicles in the gradient, and both technologies are available to best isolation technology. In addition to these traditional isolation techniques, easy-to-use precipitation solutions, such as ExoQuick™ and Total Exosome Isolation™ (TEI), that have been commercialized reduce the need for expensive equipment or technical know-how. Although their mode-of-action has not been disclosed or validated, these kits are commonly used.

Figure 23:
FIG. 23 is a representative photograph of the final packaging.

Once the mixture is completed, the method can include additional steps. This leads to the use of a bone blend 102 shown in FIGS. 23 and 24, preferably from the same vertebral bone or at least bone from the same donor.

When the mixture is prepared, it can have whole cells exclusively, or in combination, or even no whole cells, but will have the mechanically selected non-whole cellular components including vesicular components and active and inactive components of biological activity, cell fragments, cellular excretions, cellular derivatives, and extracellular components.

In one embodiment, the infused bone fiber composition includes the sheets or mats into which the whole cells can be added. In that embodiment, it is possible to also provide bone particles with the whole cell either in a mixture or separately to be combined at the time of use.

Figure 24:
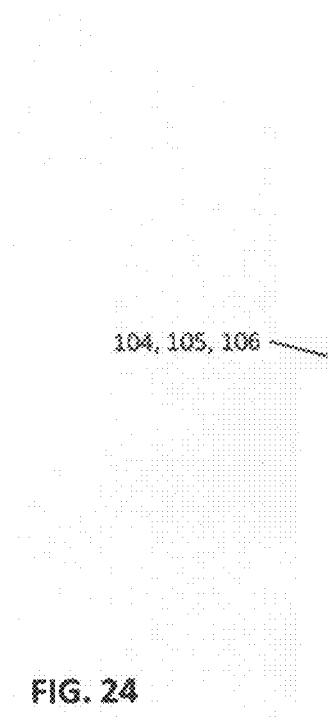
FIG. 24 is a photograph showing the ground bone.
Figure 25:
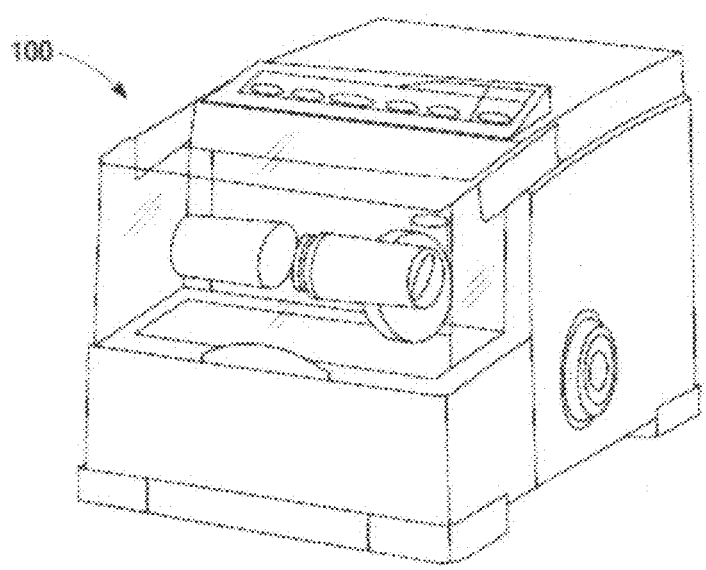
FIG. 25 is a photo of an exemplary cryomill.

In one embodiment, the bone is ground to a particle size of 100-300 µm, see FIG. 24. The bone mixture has 1.5 cc of mineralized cancellous bone 104, 1.5 cc of mineralized cortical bone 105 and 2.0 cc of demineralized cortical bone 106 yielding 30 percent, 30 percent and 40 percent respectively of the total 5 cc (5 gram) of bone material 102. The ranges coincide with the 1 cc of mixture when resuspended in 3 cc of saline to provide a bone particle and mixture for implantation, which can be by packing, injection, scaffolding or any other suitable means, into a patient in a fracture healing procedure, by way of example.

Other ranges of bone particle sizes and mixtures can be employed depending on the application which, in this example, was bone regeneration. Lower volumes and concentrations may be more suited for less intrusive bone repairs or more if larger amounts of material are needed as in a hip defect or repair.

A cryopreservation liquid according to the invention is obtained by dissolving a polymer such as poly-lysine in physiological solutions by 1-50 w/w %; preferably by 2-20 w/w %, particularly preferably by 3-15 w/w %, and more preferably by 5-10 w/w %. The physiological solutions to be used are a physiological saline as well as culture media for culturing various cells and tissues. For example, Dulbecco-modified eagle MEM culture medium (DMEM) may be one of the preferable culture media. In place of, or in addition to poly-lysine, polyallylamines may be used. In place of these, or in addition to at least one of these, a compound(s) to be used is/are selected from other polyamines such as amino-group-introduced polysaccharides, and poly-amino acids such as poly-arginine, poly-glutamic acid and poly-aspartic acid; also a polysaccharide compound(s) that is/are selected from dextran, dextrin, pullulan and chitosan as well as polycarboxylic acid such as polyacrylic acid.

Among these polymers, preferable are polymers having a structure obtainable by polymerization of a monomer compound(s) that have both cationic and anionic substituent groups within the same monomer molecules; and especially preferable is poly-amino acids. In other words, especially preferable is a polymer having a repeating unit that has both amino and carboxyl groups. Poly-lysine to be used can be either ε-poly-L-lysine or ε-poly-D-lysine or α-poly-L-lysine. Cryoprotectant polymers have molecular weights between 100 and 100,000. The most preferable polymers fall into a group of ε-poly-L-lysine routinely used as food additives. These are either synthesized by enzymes or produced by the *Streptomyces* fungi and have the average molecular weights of 1000-20,000, and particularly those of 1000-10,000 with polymerization degrees ranging between 15-35, and those with 20 or lower are attempted to be produced. The average molecular weights or the average polymerization degrees are easily measurable by sodium dodecyl sulfate-polyacrylamide gel electrophoresis (SDS-PAGE), by using an electrophoresis apparatus as a means of evaluating density. Standard protein markers are used for the measurement. The poly-lysine may be heat-treated to increase its molecular weights greater than 30,000 and used as the polymer compound. However, the molecular weight range mentioned above is preferable due to the increasing viscosity with molecular weight. Because the poly-lysine having a free terminal carboxyl group has side-chain primary amino groups, their partial amidation by dicarboxylic anhydrides greatly gives excellent miscibility and solubilization performance described later. Other particularly favorable polymer compounds also adoptable according to the invention are polyallylamines with average molecular weights of 1000-1,000,000, preferably 1000-20,000. For examples, such adoptable polymers are: aqueous solution of the allylamine polymer (PAA-03 of Nitto Boseki Co., Ltd.) added with acetic anhydride or acetic acid; and the partially-methoxy-carbonylated allylamine polymer (PAA-U5000 of Nitto Boseki Co., Ltd.). The allylamine polymer, in same manner with the poly-lysine, has as side-chain groups primary amino groups only, but density of the primary amino group per unit molecular weight is larger in the allylamine polymer than in the poly-lysine. And, when the allylamine is partially carboxylated, obtained polymer compound is considered to act in same manner with partially-carboxylated poly-lysine mentioned later.

Preferably, the amino groups of the polyamine are partially blocked by being carboxylated or acetylated with carboxylic acid anhydride(s). This blockage is done by the carboxylation or acetylation of the amino groups to the degrees of preferably 50-99 mol %, particularly 50-93 mol %, more preferably 50-90 mol %, still more preferably 55-80 mol %, and the most preferably 58-76 mol %. About 50% of the amino group would be blocked by being reacted with 52-53 mol % of anhydrous carboxylic acid on basis of molar amount of the amino groups in the polyamine. In a normal reaction condition, 90-95% of the amino groups would be blocked when reacted with 100 mol % anhydrous carboxylic acid. The blocking rates above or below the above-mentioned ranges would decrease cryopreservation effects. Carboxylic acid anhydrides adoptable herein include acetic anhydride, citric anhydride, succinic anhydride, glutaric anhydride, malic anhydride, fumaric anhydride and maleic anhydride. Among these, succinic anhydride and acetic anhydride are particularly preferred.

However, polyamine with amino groups not blocked as free may also be used; thus adoptable are the degrees of carboxylation and acetylation throughout a range of 0-100 mol/mol %. In the present invention, polycarboxylic acid in which a part of the carboxyl groups is aminated may be used. More specifically, polycarboxylic acid may be partially aminated by reacting its carboxyl group with compounds such as diamine, triamine and the polyamine. Adoptable diamines are ethylenediamine and hydrazides such as adipodihydrazide. Reaction of these amino compounds with carboxylic acid is by way of addition reaction with carbodiimide. In such occasion, adoptable is the degree of amination in a range of 0-100 mol/mol %. In same manner with blockage of amino groups, percentage of remaining carboxyl groups is preferably in a range of 50-99 mol %, more preferably in a range of 60-97 mol %, in each of which remaining percentage is for aminated carboxylic groups. For example, polyacrylic acid having average molecular weights of 1000-3,000,000, or 1000-10,000 in particular, is used; and 1-50 mol % of, preferably 3-40 mol % of, carboxyl groups of the polyacrylic acid are blocked with amines and carbodiimides such as ethylenediamine dihydrazide, or the like. Cryopreservation liquid according to the invention may also contain 0.3-15 w/w %, or 0.1-50 w/w % in particular, of conventional cryoprotectant materials such as DMSO, glycerol, ethylene glycol, trehalose or sucrose. Because cells are subject to damages caused by the oxidation stress during freezing and thawing, the addition of anti-oxidants to the cryoprotectant is expected to improve its preserving effects. For examples, anti-oxidants such as catalase, peroxidase, superoxide dismutase, vitamin E, vitamin C, polyphenols such as epigallocatechin gallate or glutathione may be used.

The osmotic pressure of the cryopreservation agent according to the invention is 200-1000 mOsm/kg, more preferably is 300-700 mOsm/kg, and further preferably 400-600 mOsm/kg. The cryopreservation agent according to the invention is applicable to the preservation of not only cells but also tissues. Examples of such cells and tissues to be cryopreserved by the cryopreservation agent are cultured cell lines, fertilized eggs of animal and human origin. Further examples are sperm cells, embryonic stem cells, IFS cells, mesenchymal stem cells, haemopoietic stem cells, neuronal stem cells, umbilical cord blood stem cells, hepatocytes, nerve cells, cardiomyocytes, vascular endothelial cells, vascular smooth muscle cells and blood cells. Not only animal or human cells but also plant cells can be included. Tissues and organs that are able to be preserved by the cryopreservation agent according to this invention are skins, nerves, blood vessels, cartilages, cornea, livers, kidneys, hearts and pancreatic islets.

Additional novelty of this invention is afforded in the variation in osmolality invigorated during the sublimation process. The loss of water suspends the materials in a static and transient state of relative harmony. With rehydration in the use of the product in saline, or in patient care, or in common practice of combination with other allografts, differences extant to the original formulation are extended to new metabolic demands. Variations in shape and thickness and absorption will define the destiny of whole, fragment, coated, fractured, and cellular organelles.

An interesting aspect of the present invention is the ability to adjust the pH from the preferred range of 7.4 to greater or lesser amounts. This allows the electro field charge to be adjusted greater or lower as a tailored means of increasing or decreasing the predetermined time for the coating to be metabolized. Alternatively, the mixture and the protectant can be diluted prior to implantation with sterile water or saline or host blood to thin the protectant coating to shorten the time to be metabolized if so desired. In any event, the present invention insures no rinsing or separation of the protectant from the cells is required insuring much higher survivability of the donor mixture.

Current understanding advanced in this continuation is adapted to note that once frozen, the material can be thawed, sublimated through a process of cryo-lyophilization, and that various concentrations of bone marrow collections of whole cells, cell fragments, exosomes, secretome packages, and free cytokines can be produced and admixed with allograft materials.

Such collected materials are stable at temperatures above freezing, and can be further combined with synthetic and organic polymers, embedded in fibers, electrospun in fleece, adsorbed and absorbed by allografts, and used within the scope of biologic protection with minimal manipulation.

These processes can also be used to prepare a dense, bioactive derivative that can be mixed as a contribution to hydrogel cartridge technologies. Given the categorization of the polyampholyte as a hydrogel, the combination offers room temperature considerations to additive manufacturing technologies using bio inks. Printability of a biomaterial is determined by the printing technique. Although a wide range of biomaterial inks including polymers, ceramics, hydrogels and composites have been developed, the field struggles with processing these materials into self-supporting devices with tunable mechanics, degradation, and bioactivity. The development of an allograft laden hydrogel affords such potentials.

The current invention defines a bone grafting material principally defined by long aspect ratio fiber morphology derived from cortical bone that has been either surface or partially or fully decalcified or demineralized and subsequently infused with non-whole cell supernatant derived from fatty and cellular marrow, stromal vascular fraction, interstitial fluid, and free water content supporting skeletal tissue. The collagen, and non-collagenous proteins, lipids, and amino acids infused into the grafting material may be further protected by infiltrating a polyampholyte cryoprotectant, or combinations of polyampholyte cryoprotectant with supernatant that are similarly infused prior to being formed, shaped, or cryo-lyophilized. Cortical bone fibers fabricated by this technology can be matted, molded, woven, braided, embossed with mimetic topography, stacked to create laminates, further combined with cells fully differentiated to osteocyte phenotype, or stem cells retaining multilineage potential to support restitution of bone tissue deficits, or sustain regeneration of bone morphology following traumatic damage. The infused matrices can be fabricated as stacked laminate. varying in thickness and charge attendant to polyampholytes composition. The stacked lamina individually assemble or define a resultant charge potential in conjunction with the plied depth of the material and proportional to the specific polyampholyte charge concentrations used in each. In example, matted, rolled, flattened, or embossed materials, develop zeta potential by design and offers analog mimetic as a non-digital remedy to guide biochemical equilibrium when tissues are rewetted. Essentially, this invention defines a gradient of growth factors, non-whole cell constituents, polyampholyte charge, combinations with cells, and an electrically motile graft material. By intention the marrow constituency effecting equilibrium between stroma, cell, interstitial fluid and mineralized bone is guided to direction and dimension of the invention. Following decalcification and processing, the assets separated during process are reintegrated to approach the whole of the original tissue. Surface demineralization to depths varying by individual tissue guides a complex process of cellular-mechanical behavior that is challenging to fully understand but important to consider. In part it has long been accepted that the origin of organic matrix shear yield stresses results from extant mineralization stresses. In the context of a fibers or micronized cortical components, the compressive stresses are likely to push the collagen molecules together and make them more closely packed in in the direction of the force. Given the compression in shear, the expectation of frictional forces inside the organic matrix is well known in cartilage and other tissues where avoiding shear is critical to their performance. Disturbing collagen fibrils accentuates the surface forces, contact pressures, and subsequent risk of accelerated degeneration in these tissues but in context of seeking osteoinductivity and heightened turnover, the process hastens the active engagement of regenerative integration.

The loss of organic matrix with mineral content and larger frictional forces, reduces larger shear load transfer before slippage. Once the shear forces overcome frictional forces on the collagen molecules and/or collagen fibrils, the collagen molecules and/or fibrils start to slip relative to one other, creating shear yield in bone matrix. In the microenvironment of a void filling allograft, the differential thickness of the matrix demineralization offers surface deformations due to applied external loads that are proportional to the partial demineralization. In addition to altering the fibrillar orientation and packing of the collagen molecules, it is known in the art that the bioactivity of the bone growth factors is labile in proportion to the demineralization of the matrix. In combination, the surface demineralization enhances shear, the lack of mineral permits more osteoinductive factors to be available, and as these changes take place at the fibrillar level, the number of interactions and their intensity among the collagen molecules provides a unique differential that is infinitely variable by design.

Inorganic additions to fibers or to surface demineralized micronized bone: within the scope of embodiments, broad potential resubstituting following demineralization might be considered. Known assets to be considered advance the art beyond elemental inclusions as ceramics evolve as high technology applications such as energy conversion, environmental control, sensors, electronics, and healthcare sectors to name but a few. While the fabrication of traditional articles can be carried out by pressing wet clay, advanced ceramics integrated as components of bioactive compounds are singularly unique from current biomaterials.

In example, polymer-derived ceramics offer composite resonance that lend to composition-structure-property relationships. Although this underscores the context of bone with organic collagens and proteins supporting and directing the location and size of apatite crystals to solidify bone, production efficiencies assume far greater importance in considering how raw material characteristics and process parameters can be used to fully affect structure-property relationships.

In description, this invention invigorates the opportunity to displace, replace, or reorganize biologic materials matrix composites that can provide a lead-free dielectric, or piezo, or oxide, or ceramic substrate that further optimizes medical device ceramics (e.g., calcium phosphate cements, porous scaffolds for bone replacement, bioglasses, and ionomer cements). Less specifically and more broadly, combinations of silica, calcium oxide, sodium oxide, and phosphorous pentoxide, and additional elements that would be considered adjunct to enhanced bone and bioactive ceramics would include ortho-calcium phosphate, tetra-calcium phosphate, and hydroxyapatite are materially possible to introduce back into bone. Other families including borates, magnesium oxide, potassium oxide, sodium oxide, calcium fluoride, barium titanate, and carbonates in bone separate and inclusive from apatites. Still other options for removal could include a distillation of decalcification, a dialysis exchange, and resolubilizing the bone salts for recombination with either supernatant marrow, polyampholyte protectant, or other bone compositions that render in whole in composition and function.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A method of making infused demineralized bone fibers comprises:
    cutting or shaving whole bone into bone fibers;
    washing the bone fibers;
    demineralizing the bone fibers; and
    infusing the demineralized bone fibers with a biological mixture of a supernatant of biologic material and a polyampholyte cryoprotectant to create infused demineralized bone fibers, the biological mixture may further comprise an optional buffy layer containing whole cells;
    wherein the step of infusing includes exposing the demineralized bone fibers to a negative pressure or vacuum to draw the biological mixture and the polyampholyte cryoprotectant into the bone fibers and thereafter exposing the demineralized whole bone to a positive pressure to drive the biological mixture and the polyampholyte cryoprotectant into the bone fibers;
    freezing the infused demineralized bone fibers; and
    drying the infused demineralized bone fibers, wherein the step of drying includes freeze-drying by lyophilization, wherein the whole cells, if any, have a membrane with a contents of the whole cells, the membrane being ruptured during processing, wherein the infused demineralized bone fibers are storable at ambient or room temperature suitable for implantation with no rinsing or washing, the infused demineralized bone fibers being rehydrated and diluted prior to implantation into a patient in need of bone regeneration and repair.

2. The method of claim 1 wherein the bone fibers have a length of 1 cm to 30 cm.

3. The method of claim 1 wherein the step of cutting or shaving includes passing the whole bone through a cutting die to form shaped long bone fibers.

4. The method of claim 3 wherein the shaped long bone fibers have a trapezoidal or triangular cross-section.

5. The method of claim 1 further comprises one or more of the steps of shaping, extrusion, molding or flattening the dried bone fibers into sheets to form random fiber stacked matting.

* * * * *